United States Patent
Lu et al.

(10) Patent No.: US 12,178,449 B2
(45) Date of Patent: Dec. 31, 2024

(54) LATERAL SLEEVE PIPE DRILL AND OPERATING METHOD

(71) Applicant: Beijing Longfu Hospital, Beijing (CN)

(72) Inventors: Yanli Lu, Beijing (CN); Yuanli Wang, Beijing (CN); Qingpu Wang, Beijing (CN); Zhijun Tian, Beijing (CN)

(73) Assignee: BEIJING LONGFU HOSPITAL, Beijing (CN)

( * ) Notice: Subject to any disclaimer, the term of this patent is extended or adjusted under 35 U.S.C. 154(b) by 392 days.

(21) Appl. No.: 17/621,444

(22) PCT Filed: Jun. 12, 2020

(86) PCT No.: PCT/CN2020/095913
§ 371 (c)(1),
(2) Date: Dec. 21, 2021

(87) PCT Pub. No.: WO2020/259324
PCT Pub. Date: Dec. 30, 2020

(65) Prior Publication Data
US 2022/0346808 A1    Nov. 3, 2022

(30) Foreign Application Priority Data
Jun. 26, 2019 (CN) .......................... 201910562187.7

(51) Int. Cl.
*A61B 17/16* (2006.01)
(52) U.S. Cl.
CPC ...... *A61B 17/1633* (2013.01); *A61B 17/1622* (2013.01)

(58) Field of Classification Search
CPC . A61B 17/1637; A61B 17/17; A61B 17/1703; A61B 17/1707; A61B 17/171;
(Continued)

(56) References Cited

U.S. PATENT DOCUMENTS

| 5,253,659 A | * | 10/1993 | McNamara | ............ A61B 17/34 128/898 |
| 5,885,300 A | * | 3/1999 | Tokuhashi | ............ A61F 2/4611 606/104 |

(Continued)

FOREIGN PATENT DOCUMENTS

| CN | 203861305 U | 10/2014 |
| CN | 204033390 U | 12/2014 |

(Continued)

*Primary Examiner* — Eric S Gibson
(74) *Attorney, Agent, or Firm* — Shumaker, Loop & Kendrick, LLP; James D. Miller

(57) ABSTRACT

The present disclosure relates to a lateral sleeve pipe drill and a operating method, belong to the field of surgical instrument technologies, and solves the problems that a bone passage cannot be effectively corrected and is liable to be corrected excessively, and correction is time-consuming and damages important functional bone tissue morphology. The lateral sleeve pipe drill is of a hollow cylindrical shape and includes a first end and a second end. An outer wall of the first end is provided with a correction portion for correcting the bone passage. The first end is arranged in a human body and is of a particular shape adapted to different surgical methods, a surgical approach direction, and a human body internal structure.

7 Claims, 10 Drawing Sheets

(58) Field of Classification Search
CPC ............ A61B 17/1714; A61B 17/1717; A61B 17/1721; A61B 17/1725; A61B 17/1728; A61B 17/1732; A61B 17/1735; A61B 17/1739–1792; A61B 17/1796
See application file for complete search history.

(56) References Cited

U.S. PATENT DOCUMENTS

| | | | | |
|---|---|---|---|---|
| 5,951,561 | A * | 9/1999 | Pepper | A61B 17/1717 606/86 R |
| 5,954,671 | A * | 9/1999 | O'Neill | A61B 17/1637 606/179 |
| 6,416,518 | B1 * | 7/2002 | DeMayo | A61B 17/1735 606/98 |
| 6,620,180 | B1 | 9/2003 | Bays et al. | |
| 10,729,478 | B1 * | 8/2020 | Watts | A61B 17/864 |
| 2003/0195392 | A1 * | 10/2003 | Hamel | A61B 17/3417 600/213 |
| 2004/0243138 | A1 * | 12/2004 | Cole | A61B 17/72 606/99 |
| 2009/0105775 | A1 * | 4/2009 | Mitchell | A61B 17/3472 606/86 R |
| 2011/0295210 | A1 | 12/2011 | Wright | |
| 2014/0257418 | A1 * | 9/2014 | Arthur | A61B 50/20 606/86 R |
| 2016/0235451 | A1 * | 8/2016 | Johnston, Jr. | A61B 17/808 |
| 2017/0056040 | A1 * | 3/2017 | Vetter | A61B 10/0233 |
| 2020/0268361 | A1 * | 8/2020 | Ty | A61B 17/1635 |
| 2020/0367914 | A1 * | 11/2020 | McGillicuddy | A61B 17/1637 |
| 2022/0240997 | A1 * | 8/2022 | Krause | A61B 17/8625 |

FOREIGN PATENT DOCUMENTS

| | | |
|---|---|---|
| CN | 106236187 A | 12/2016 |
| CN | 106264653 A | 1/2017 |
| CN | 208640780 U | 3/2019 |
| CN | 208769898 U | 4/2019 |
| CN | 110179522 A | 8/2019 |
| CN | 210749383 U | 6/2020 |
| KR | 20130003618 U | 6/2013 |

* cited by examiner

LATERAL SLEEVE PIPE DRILL AND OPERATING METHOD

CROSS-REFERENCE TO RELATED APPLICATION

The present application is a national stage application of International Patent Application No. PCT/CN2020/095913, which is filed on Jun. 12, 2020, and claims the priority of Chinese patent application No. 201910562187.7, which is filed on Jun. 26, 2019, entitled "Lateral Sleeve Pipe Drill and Operating Method", which is incorporated in its entirety herein by reference.

TECHNICAL FIELD

The present disclosure relates to the technical field of surgical instruments, in particular to a lateral sleeve pipe drill and a method for operating the same.

BACKGROUND

Bone hyperplasia occurs mostly in middle-aged people and older. It is generally believed that due to physical weakness and degenerative changes after middle age; if a person stands or walks for a long time and holds a certain posture for a long time, due to muscle traction or avulsion, bleeding, hematoma organizing, thorn-like or lip-like bone hyperplasia, also known as bone spurs or rigid osteophytes. Intervertebral disc herniation, Asian populations often have spinal stenosis, osteophytosis, and nerve root adhesions. Spinal endoscopic treatment has become an important surgical approach for spinal diseases, and minimally invasive spinal combined treatment has a bright future. When performing spinal endoscopic treatment, it is often necessary to adjust a position and an angle of a bone passage during a surgery.

In a process of delivering a surgical instrument into a patient's body, to protect the nerves, it is necessary to ensure that nerves are within a field of view of an endoscope. However, due to pathological changes, nucleus pulposus compresses nerves, or a mutation of the nerves itself cause the nerves to deviate from its original position, making it impossible to see the nerves in the endoscope. Therefore, it is necessary to ream, that is, to correct the bone passage so that an angle of the endoscope can be adjusted to find the nerves.

In the prior art, an electric drill is generally used to correct the bone passage, that is, to grind off osteophytosis by 1-2 mm. Since outer walls of tools, endoscopes and other instruments used in the surgery are cylindrical, the passage needs to be corrected to a circular arc shape. However, the electric drill can only correct the passage to a plurality of discontinuous arcs, but cannot correct the passage to a continuous and relatively regular arc. As a result, the angle of the surgical instrument cannot be adjusted, and it is difficult to find the nerves by the endoscope. In addition, if the electric drills are used to correct the bone passage, the bone passage can be easily over-corrected and damage internal bony tissues.

In the prior art, the bone passage is corrected by arranging the front end of the sleeve pipe drill in a sawtooth shape, but a problem that the bone passage cannot be corrected to a continuous and relatively regular arc so that the angle of the surgical instrument cannot be adjusted is also provided. In addition, a problem that the amount of grinding is not easy to control is also provided.

SUMMARY

In view of the forgoing analysis, the present disclosure aims to provide a lateral sleeve pipe drill and an operating method to solve the problem that a bone passage in the prior art cannot be effectively corrected and is liable to be corrected excessively, and correction is time-consuming and damages important functional bone tissue morphology.

An objective of the present invention is realized through the following technical solutions:

In one aspect, the present disclosure provides a lateral sleeve pipe drill. The lateral sleeve pipe drill is of a hollow cylindrical shape and includes a first end and a second end. The outer wall of the first end is provided with a correction portion for correcting the bone passage. The first end is arranged in a human body, and is of a shape adapted to different surgical methods, the surgical approach direction and the internal structure of the human body. The second end is provided with a submersible handle to supply power to correct the bone passage. The submersible handle includes a grip portion and a handle body. The handle body is provided with a passage into which the lateral sleeve pipe drill enters. A side wall of the handle body is provided with an opening through which the lateral sleeve pipe drill enters the passage. The lateral sleeve pipe drill is partially arranged in the submersible handle.

On the basis of the above solution, the present disclosure has made the following improvements:

In some embodiments, the passage includes an oblique passage and a central passage arranged coaxially. The oblique passage and the central passage are arranged in a spiral structure in sequence. The central passage has a C-shaped cross-section. At least one of the central passage and the lateral sleeve pipe drill is provided with a fixing portion. The fixing portion is configured to fix the lateral sleeve pipe drill and the submersible handle.

In some embodiments, the shape is of oblique-type, double-forked-type, duck-tongue-type or semi-elliptical-type.

In some embodiments, a side wall of one fork of the double-fork type lateral sleeve pipe drill is provided with the correction portion, and a side wall of the other fork is not provided with the correction portion.

In some embodiments, the correction portion is one of one-way thread, cross-thread and emery.

In some embodiments, the one-way thread is a horizontal thread or an oblique thread.

In some embodiments, the inner wall of the central passage is provided with a groove for accommodating and fixing the lateral sleeve pipe drill, and the groove is arranged in a direction parallel to the central axis of the central passage.

In some embodiments, a side wall of the lateral sleeve pipe drill in one direction is provided with a buckle adapted to a shape of the passage, and the buckle is configured to fix the lateral sleeve pipe drill and the submersible handle.

On the other hand, the present disclosure also provides a method for operating a lateral sleeve pipe drill, including the following steps:

Step 1: determining a direction and a path that a surgical instrument needs to enter;

Step 2: placing the lateral sleeve pipe drill at a position where the bone passage needs to be corrected;

Step 3: manually rotating leftwards and rightwards or move the lateral sleeve pipe drill up and down, and grinding the bone passage with a correction portion on an outer wall until a surgical field is well exposed and the surgical instrument is able to smoothly pass through the bone passage to a designated position.

In some embodiments, step 3 further includes replacing lateral sleeve pipe drills with different end shapes and different types of correction portions.

The present disclosure has the following beneficial effects:

(1) In the present disclosure, a correction portion is provided on an outer wall of a first end to correct the bone passage. A degree of correction can be accurately controlled as required, and it is not easy to cause excessive correction.

(2) By arranging the lateral sleeve pipe drill into a cylindrical shape, the bone passage can be easily corrected into a continuous and relatively regular arc, thereby facilitating the passage of a cylindrical surgical instrument.

(3) By designing the first end as oblique-type, double-forked-type, duck-tongue-type or semi-elliptical-type, the lateral sleeve pipe drill of the present disclosure can be well adapted to an internal structure of a human body, thereby increasing a reaming speed, and shortening surgery time. Since a shape of an end of the lateral sleeve pipe drill adapts to the internal structure of the human body, the damage of the lateral sleeve pipe drill to other parts of the human body can be reduced during the process of correcting the bone passage.

(4) By designing the lateral sleeve pipe drill as a hollow shape, and by designing the bottom of the first end to be a blunt circular shape instead of a sharp shape, an impact of the lateral sleeve pipe drill on other tissues can be reduced in the process of correcting the bone passage, thereby alleviating suffering of a patient.

(5) In the present disclosure, a correction portion is provided on the side wall of one fork of the double-fork type lateral sleeve pipe drill for reaming, and the other fork is not provided with a correction portion on a side wall to protect important soft tissues, such as nerves, dural sac, etc., so that the double-fork type lateral drill can correct the bone passage without damaging important soft tissues.

(6) By selecting the correction portion as one-way thread, a cross-thread or emery, a reaming speed is increased and a surgery time is shortened.

(7) In the present disclosure, the submersible handle is provided at a second end, which can not only provide power for correcting the bone passage, but also prevent the lateral sleeve pipe drill from centrifugation during a reaming process, thereby causing unnecessary human injury.

In the present disclosure, the forgoing technical solutions can also be combined with each other to achieve more preferred combination solutions. Other features and advantages of the present disclosure are described in the following description, and part of advantages becomes obvious from the description, or understood by implementing the embodiments of the present disclosure. The objectives and other advantages of the present disclosure can be realized and obtained through embodiments of the specification and the content specifically pointed out in the drawings.

BRIEF DESCRIPTION OF THE DRAWINGS

The drawings are only used for the objectives of illustrating specific embodiments, and are not considered as a limitation to the present disclosure. Throughout drawings, the same reference signs represent the same components.

REFERENCE SIGNS

Figure 1:
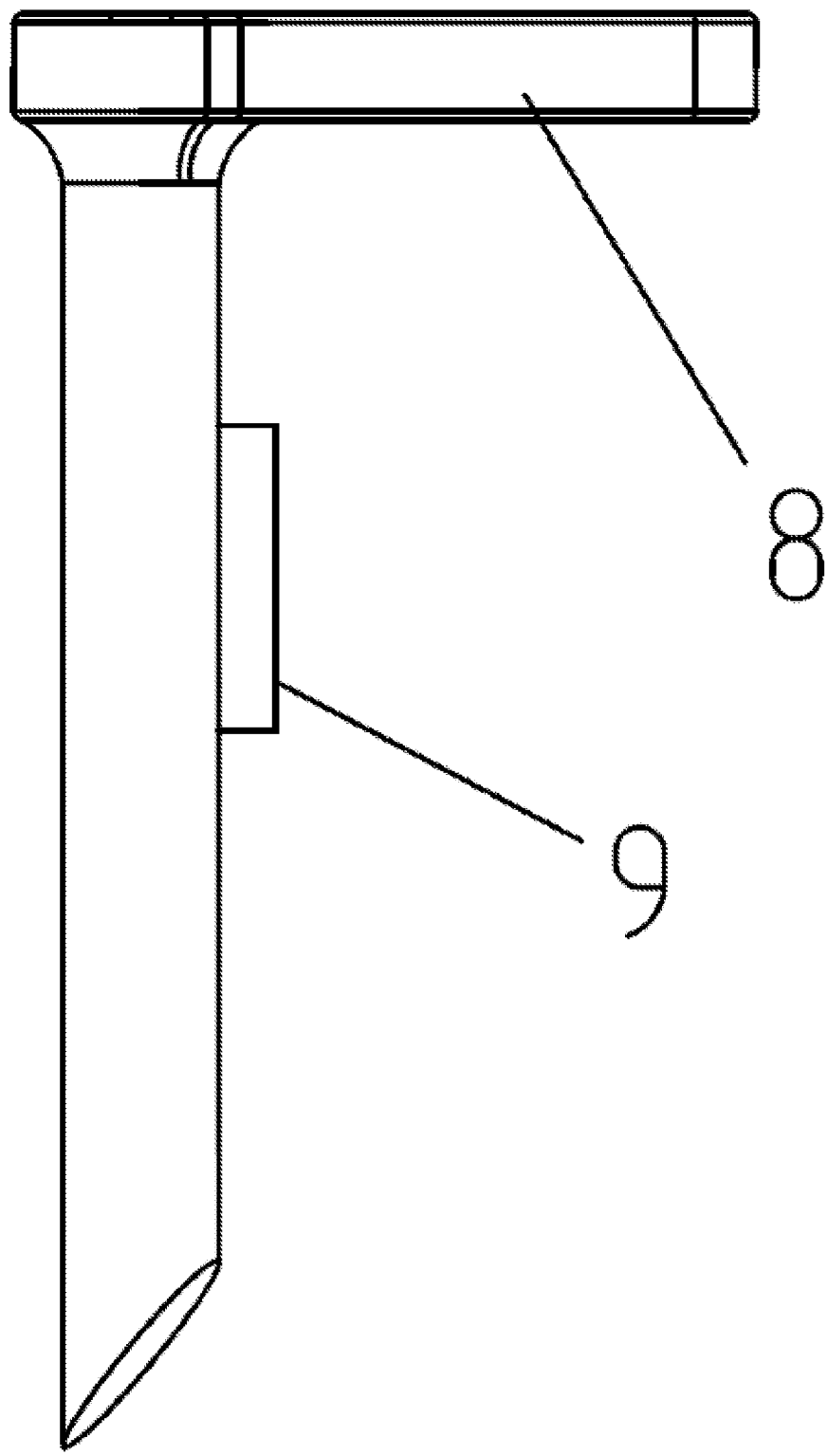
FIG. 1 is a front view of an oblique-type lateral sleeve pipe drill according to an embodiment of the present disclosure.

1: Grip portion; 2: Handle body; 3: Opening; 4: Oblique passage; 5: Central passage; 6: First groove; 7: Correction portion; 8: First handle; 9: fixing buckle.

DETAILED DESCRIPTION OF THE EMBODIMENTS

The preferred embodiments of the present disclosure are described in detail below with reference to the drawings, where the drawings constitute a part of the present disclosure and are used together with the embodiments of the present disclosure to explain the principle of the present disclosure, and are not used to limit the scope of the present disclosure.

Embodiment 1

A specific embodiment of the present disclosure discloses a lateral sleeve pipe drill, as shown in FIGS. 1-7. The lateral sleeve pipe drill is of a hollow cylindrical shape and includes a first end and a second end. An outer wall of the first end is provided with a correction portion 7 for correcting a bone passage. The first end is arranged in a human body and is of a particular shape adapted to a human body internal structure.

Compared with the prior art, the lateral sleeve pipe drill provided by this embodiment can effectively correct the bone passage, so that the surgical instrument can smoothly enter the body to reach a designated position, or expand a range of movement of the surgical instrument, broaden a field of view, and make nerves in a field of view of an endoscope, thereby avoid damaging the nerves when the surgical instrument reaches the designated position.

Specifically, the electric drill is used to modify the bone passage, which can only modify the passage to a plurality of discontinuous arcs, but cannot modify the passage to a continuous and relatively regular arc, resulting in the surgical instrument still unable to enter the body to reach the designated position. Alternatively, even if the surgical instrument barely enter the body, an angle cannot be adjusted, resulting in limited vision and unable to find nerves that deviate from original positions due to nucleus pulposus compression or nerve self-mutation. On the other hand, since only 1-2 mm needs to be corrected in a process of correcting the bone passage, the electric drill for correction can easily lead to over-correction and damage internal bony tissues. The surgery is very difficult, a risk of the surgery is very high, and a success rate of the surgery is low.

The lateral sleeve pipe drill of this embodiment corrects the bone passage by providing a correction portion on an outer wall of the first end, that is, reaming. During implementation, the lateral sleeve pipe drill extends into a part that needs to be reamed, and the correction portion of the outer wall of the first end is used to grind the bone. Grinding is performed by rotating or by moving up and down.

Considering that most surgical instruments are cylindrical, in order for the instruments to reach the designated position smoothly, the bone passage needs to be corrected into a continuous and relatively regular arc. Based on the forgoing considerations, in this embodiment, the lateral sleeve pipe drill is also configured as a cylindrical shape. Compared with other shape of the lateral sleeve pipe drill, the cylindrical lateral sleeve pipe drill is easier to correct the bone passage to the required shape, thereby improving the reaming speed and shorten the surgery time.

It should be noted that because a space for the bone passage is very narrow, a bottom of the lateral sleeve pipe drill may touch other tissues during a correction process. To reduce the impact of the lateral sleeve pipe drill on other tissues during the correction of the bone passage and to avoid damage to other tissues, the lateral sleeve pipe drill is designed as a hollow shape in this embodiment. Another reason for designing the lateral sleeve pipe drill to be hollow is that the hollow part can be placed with the endoscope, so that the surgery can be performed under full visibility.

In order to further reduce the impact of the lateral sleeve pipe drill on other tissues during the process of correcting the bone passage, and reduce the patient's pain, in this embodiment, the bottom of the first end of the lateral sleeve pipe drill is designed to be a blunt circle. Through the forgoing design, even if the bottom of the lateral sleeve pipe drill touches other tissues, serious impact is not caused, thereby effectively protecting other tissues and reducing the suffering of the patient.

Embodiment 2

Considering that the internal structure of the human body is intricate, and because of the different surgical methods and surgical approach directions, different shapes need to be designed to ensure a high reaming speed on the one hand and ensure the safety of the surgery on the other hand. The shape of the first end of the lateral sleeve pipe drill in this embodiment includes an oblique type, a double-fork type, a duck-tongue type and a semi-elliptical type, as shown in FIGS. 1-7. The lateral sleeve pipe drill of the forgoing four shapes can be well adapted to the internal structure of the human body, thereby increasing the reaming speed and shortening the surgery time. Since a shape of an end of the lateral sleeve pipe drill adapts to the internal structure of the human body, the damage of the lateral sleeve pipe drill to other parts of the human body can be reduced during the process of correcting the bone passage, thereby greatly increasing the safety of the surgery.

Figure 2:
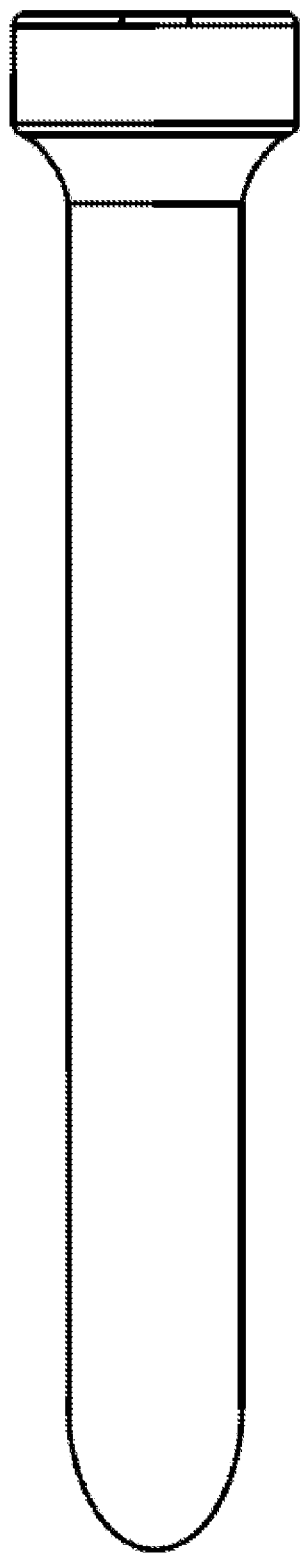
FIG. 2 is a left view of an oblique-type lateral sleeve pipe drill according to the embodiment of the present disclosure.
Figure 3:
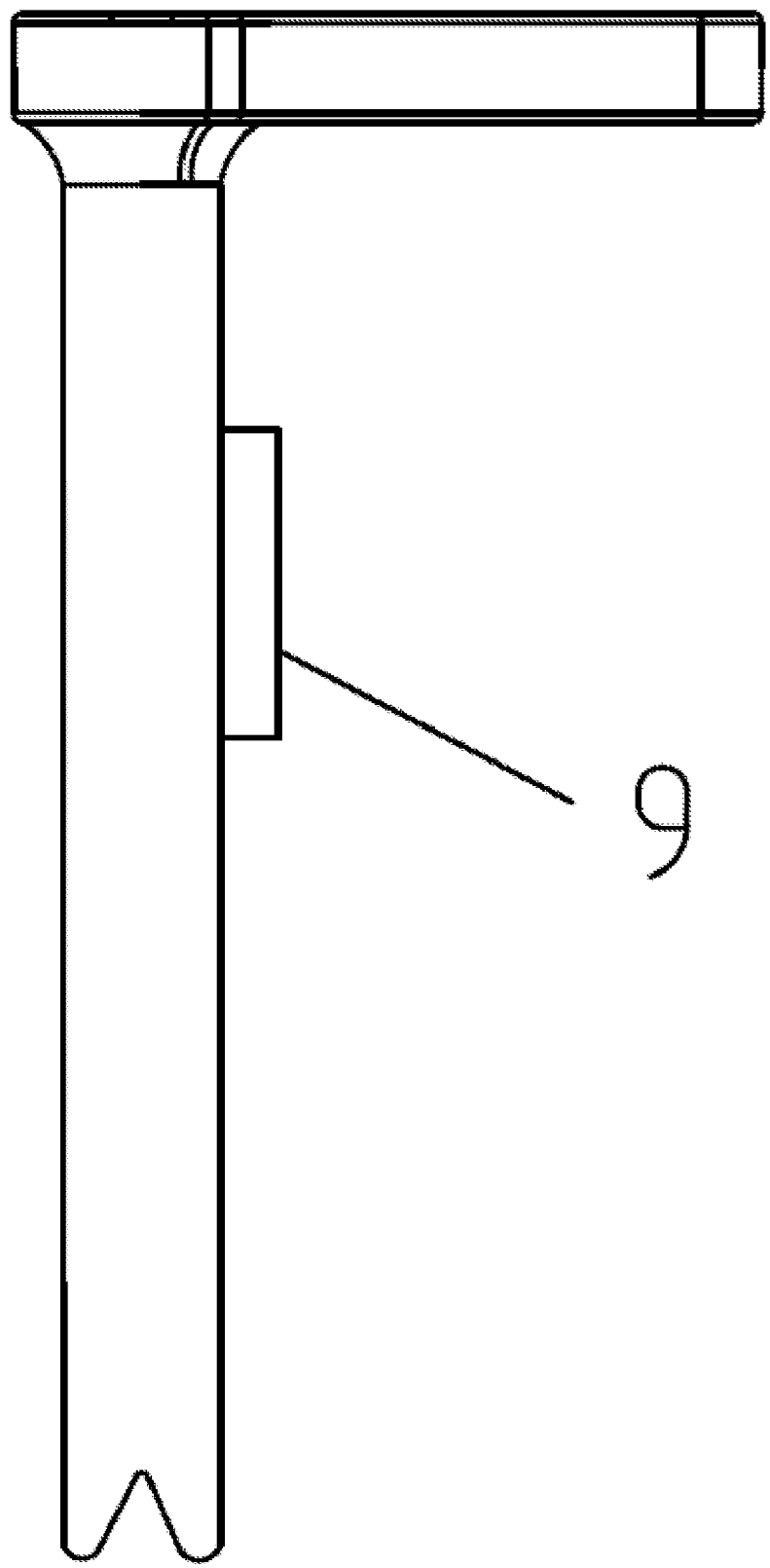
FIG. 3 is a front view of a double-fork type lateral sleeve pipe drill according to an embodiment of the present disclosure.

Specifically, the oblique type of the forgoing four shapes is relatively universal, and can be applied to most parts and a plurality of access directions, as shown in FIGS. 1-2. The double-fork type is mainly used in narrow parts such as a lateral recess and a nerve root. The lateral recess is located in a lateral spinal canal, and a front of the lateral recess is a posterior edge of a vertebral body, a back is a connection between the front of the superior articular process as well as a vertebral plate and a pedicle, and an outside of the lateral recess is an inner surface of the pedicle. A inside entrance corresponds to a front edge of a superior articular process. Lateral recesses are parts that are sunken outward on both sides of the vertebral foramen, forming a spinal nerve root passage outward and downward, continuing with an intervertebral foramen. The lateral recess is the narrowest part of a spinal canal and is a passage for the nerve root. The smaller a sagittal diameter and the larger a transverse diameter, the narrower and deeper the lateral recess. Due to a particularity of a lateral recess structure, when the bone passage at that location is corrected, the present disclosure designs a double-forked lateral sleeve pipe drill, as shown in FIGS. 3-4.

It should be noted that the double-fork type lateral sleeve pipe drill of this embodiment is only provided with a correction portion on the side wall of one of forks for grinding and reaming, and the other fork is not provided with a correction portion on the side wall for protecting important soft tissues, such as nerves, dural sac, or the like. Through the forgoing design, the double-fork type lateral sleeve pipe drill can realize the rapid correction of the lateral recess, without damaging the nerves, thereby ensuring the safety of the surgery.

Figure 5:
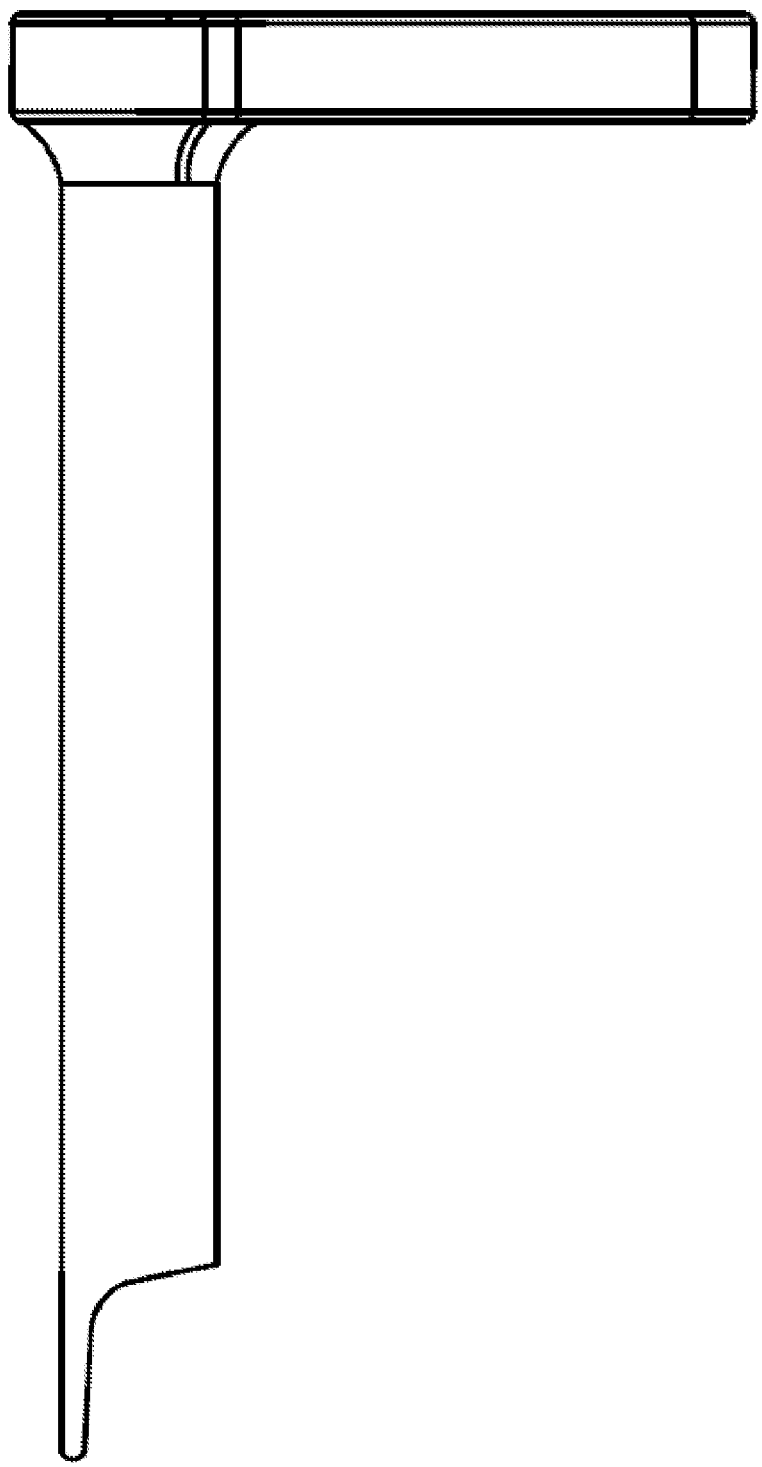
FIG. 5 is a front view of a duck-tongue type lateral sleeve pipe drill according to an embodiment of the present disclosure.
Figure 6:
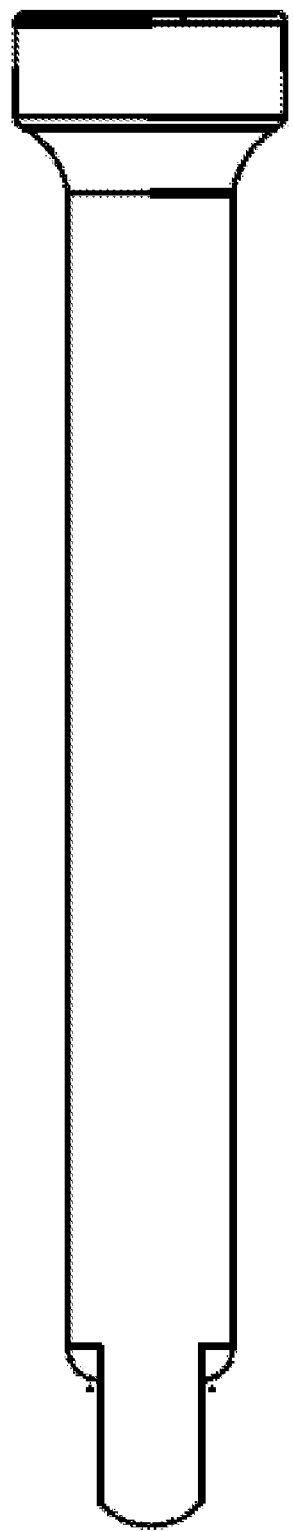
FIG. 6 is a left view of a duck-tongue type lateral sleeve pipe drill according to an embodiment of the present disclosure.
Figure 7:
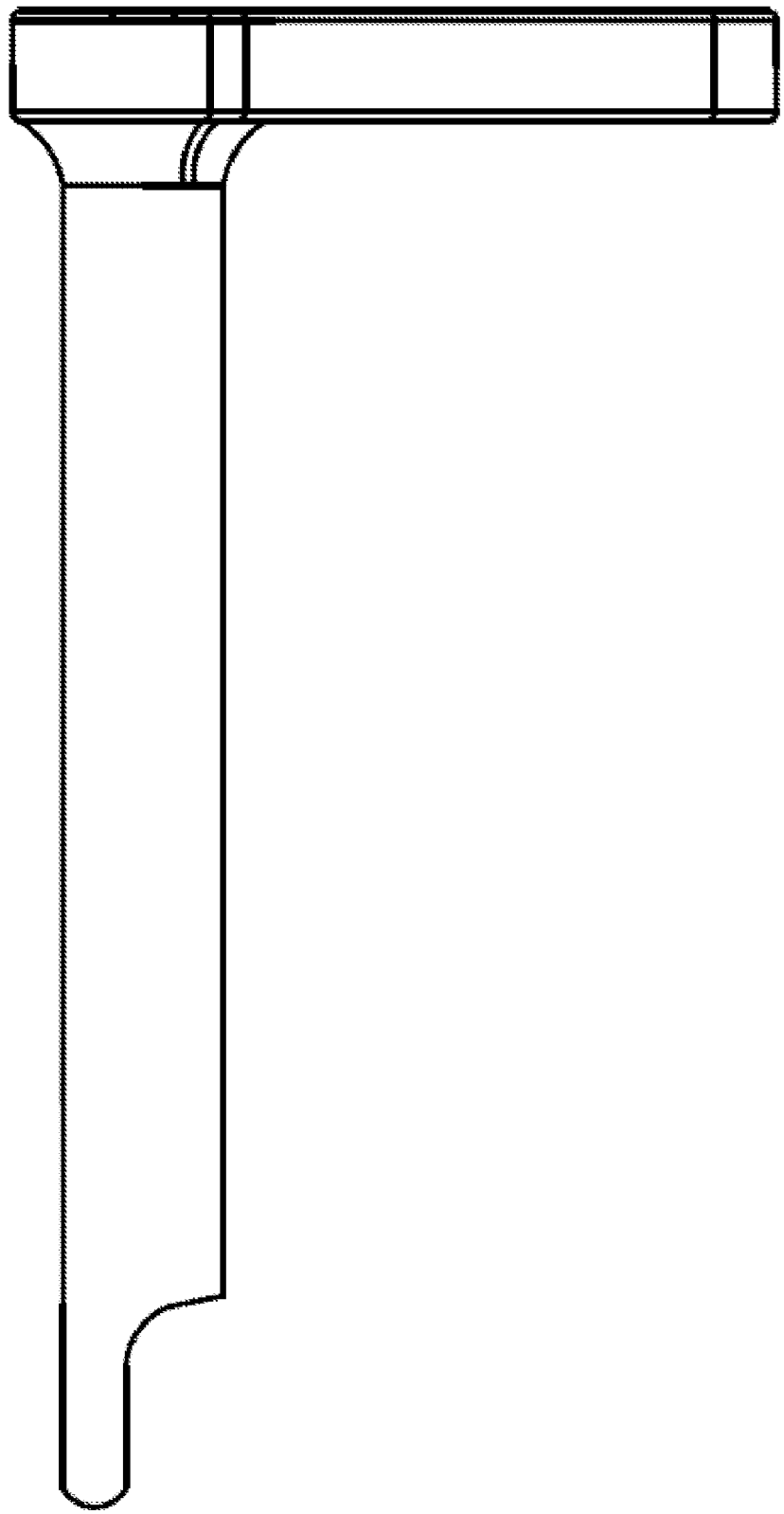
FIG. 7 is a front view of a semi-elliptical-type lateral sleeve pipe drill according to an embodiment of the present disclosure.

For the duck-tongue type lateral sleeve pipe drill, a correction portion is provided on a back for grinding, and the front end is blunt for protection, as shown in FIGS. 5-6.

Figure 4:
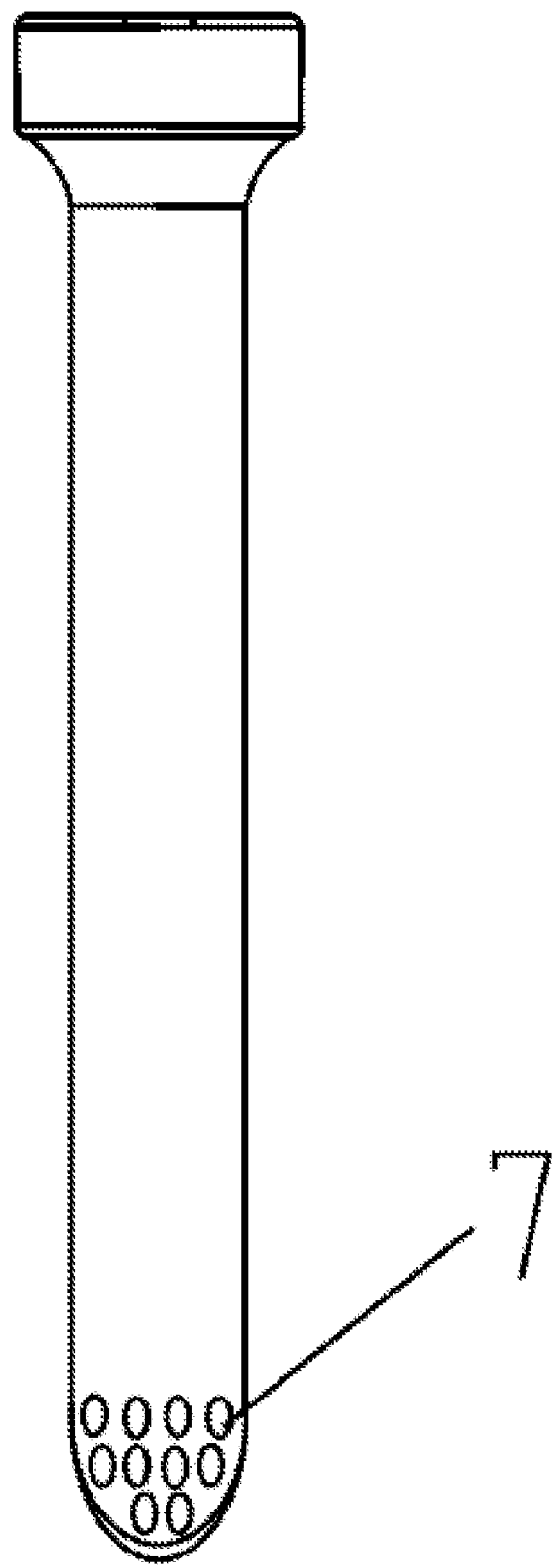
FIG. 4 is a left view of a double-fork type lateral sleeve pipe drill according to an embodiment of the present disclosure.
Figure 8:
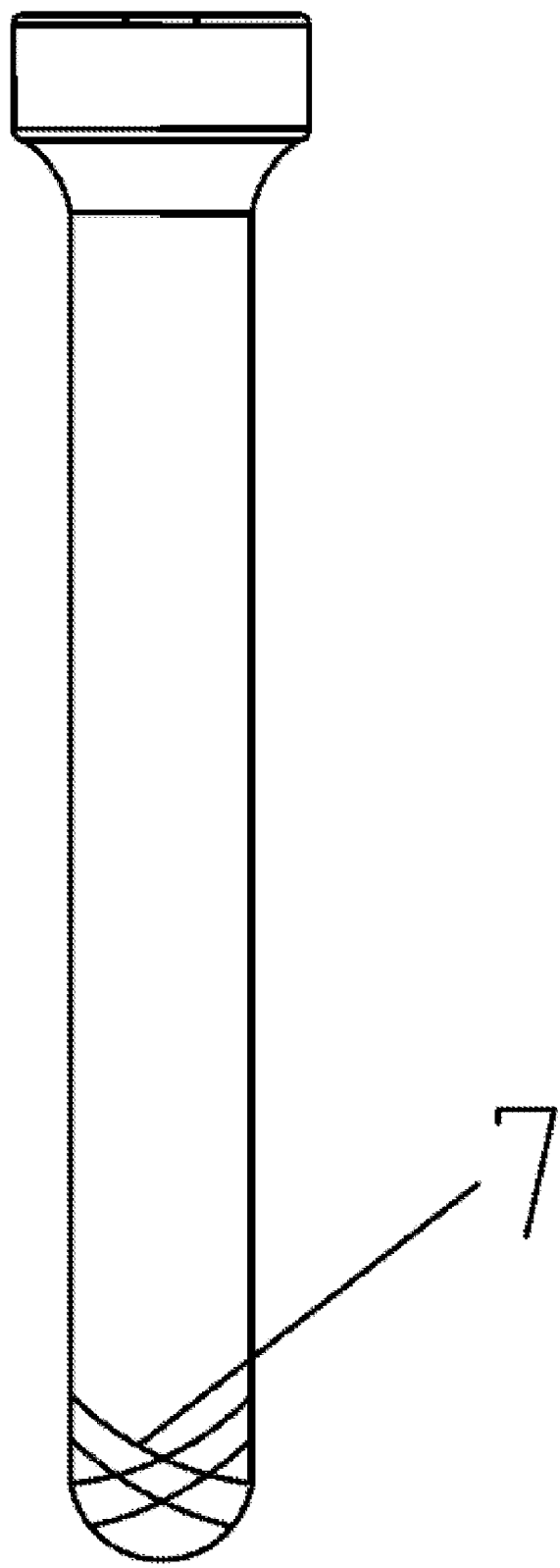
FIG. 8 is a schematic diagram of a lateral casing drill with the correction portion being the cross-threaded according to an embodiment of the present disclosure.

It should be noted that the correction portion of this embodiment may be a one-way thread, a cross-thread or emery, as shown in FIGS. 4 and 8. The one-way thread can be divided into a horizontal thread and an oblique thread. The correction portion of the forgoing structure can effectively grind the bone tissues, increase the reaming speed, and shorten the surgery time. During implementation, it is possible to replace the lateral sleeve pipe drills with different shapes and different types of correction portions according to different entering depths of the lateral sleeve pipe drill.

Considering that the amount of bony tissue that needs to be ground is very small, only a few millimeters, such as 1-2 mm, if the electric-driven lateral sleeve pipe drill is used for correction, it is very easy to cause excessive correction and severely damage the bony tissue. Therefore, the lateral sleeve pipe drill of this embodiment does not adopt electric drive, but chooses to manually operate the lateral sleeve pipe drill.

In order to facilitate holding, the second end of the lateral sleeve pipe drill is provided with a first handle 8 in this embodiment, so that it is convenient to hold the lateral sleeve pipe drill for grinding.

The lateral sleeve pipe drill provided by the present disclosure can effectively correct the bone passage on the one hand, so that the surgical instrument can smoothly enter the body to reach a designated position, or expand a range of movement of the surgical instrument, broaden a field of view, and make nerves in a field of view of an endoscope, thereby avoid damaging the nerves when the surgical instrument reaches the designated position. On the other hand, the lateral sleeve pipe drill of the present disclosure has a simple structure, low cost and easy to operate. In addition, since the amount of the bony tissues that needs to be ground is very small, only a few millimeters, compared with the electric drive to correct the bone passage in the prior art, the present disclosure uses a manual drive, which is not easy to cause excessive correction and effectively protects the bony tissue, greatly improving the safety of surgery.

Embodiment 3

Another embodiment of the present disclosure discloses a method for operating a lateral sleeve pipe drill, which is used to operate the lateral sleeve pipe drill of Embodiment 1 and Embodiment 2, including the following steps:

Step 1: determining a direction and a path that a surgical instrument needs to enter;

Step 2: inserting a surgical instrument into a passage;

Step 3: when the surgical instrument cannot be inserted smoothly or the surgical instrument can be inserted smoothly but a vision of an endoscope is not good, placing the lateral sleeve pipe drill at a position where a bone passage needs to be corrected;

Step 4: manually operating the lateral sleeve pipe drill to grind the bone passage;

Step 5: replacing the lateral sleeve pipe drill with different end shapes and different types of correction portions and continuing to grind until the surgical instrument can smoothly reach the designated position by the bone passage.

Compared with the prior art, the method of the present disclosure can effectively grind the bone tissues, increase a reaming speed, shorten a surgery time, is not easy to cause excessive correction, and greatly improves safety of a surgery. Further, the method is easy to be operated and controlled.

Embodiment 4

Figure 9:
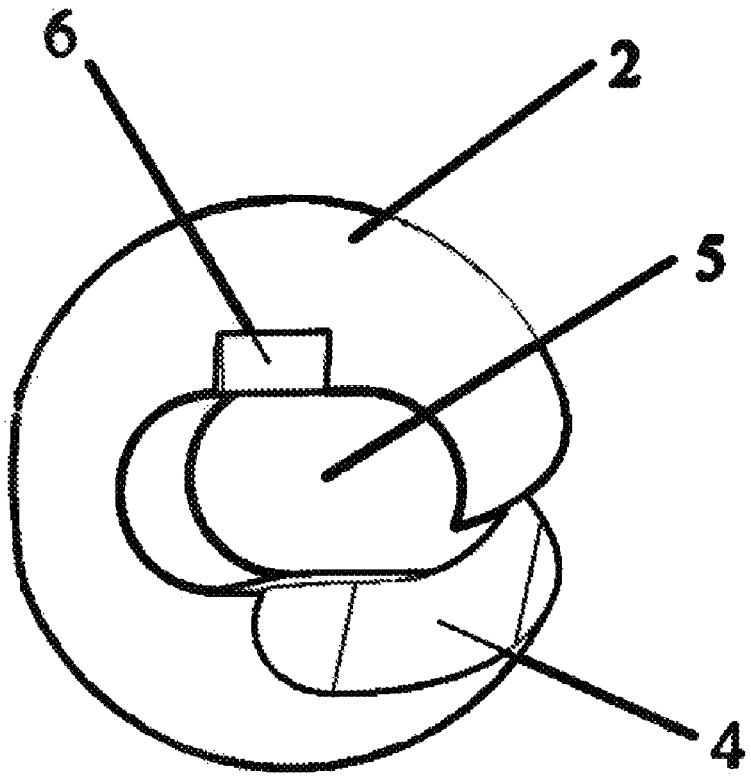
FIG. 9 is a top view of a handle body of a submersible handle.
Figure 10:
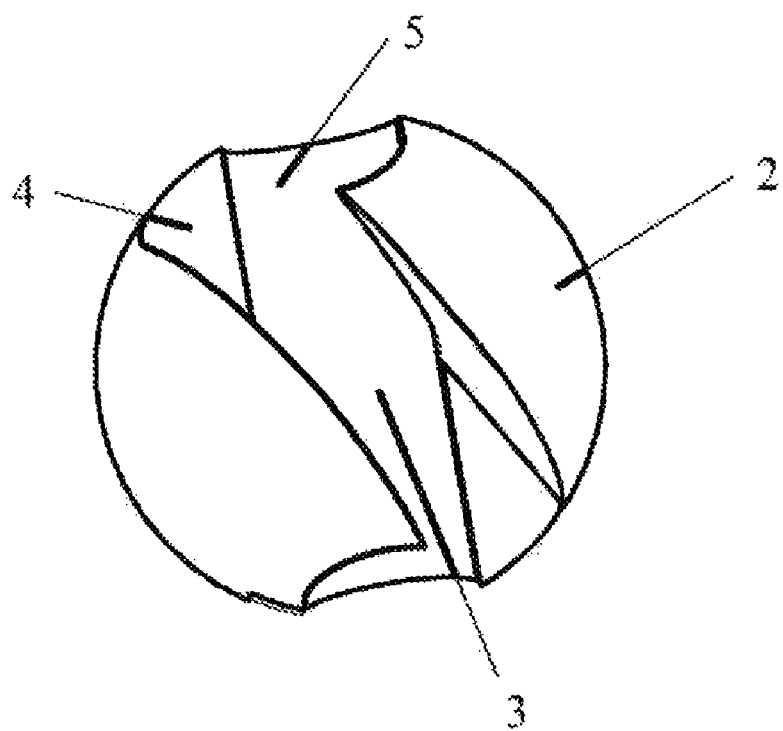
FIG. 10 is a right side view of a handle body of a submersible handle.

Another specific embodiment of the present disclosure discloses a hollow coaxial submersible handle for a spinal endoscope lateral sleeve pipe drill, as shown in FIGS. 9-10. The submersible handle includes a grip portion 1 and a handle body 2. The handle body 2 is provided with a passage into which the lateral sleeve pipe drill enters. A side wall of the handle body is provided with an opening 3 through which the lateral sleeve pipe drill enters the passage. The passage includes an oblique passage 4 and a central passage 5 arranged coaxially. The oblique passage and the central passage are arranged in a spiral structure in sequence. The central passage 5 has a C-shaped cross-section.

At least one of the central passage 5 and the lateral sleeve pipe drill is provided with a fixing portion. The fixing portion is configured to fix the lateral sleeve pipe drill and the submersible handle.

During implementation, the lateral sleeve pipe drill enters the oblique passage 4 through an opening 3 on a side wall of a handle body, and enters the central passage 5 after rotating by a certain angle, and the lateral sleeve pipe drill and the submersible handle are fixed by the fixing portion.

Compared with the prior art, the hollow coaxial submersible handle for the spinal endoscope lateral sleeve pipe drill provided by this embodiment can increase a torque and a moment arm, reduce a labor intensity of correcting the bone passage, and increase a reaming speed, shorten a surgery time and increase the safety of a surgery.

Specifically, in this embodiment, the submersible handle is designed into a plurality of passages, that is: the central passage and the oblique passage. By arranging the oblique passage and the central passage in a spiral structure in sequence, on the one hand, it can ensure that the lateral sleeve pipe drill smoothly enter the passage of the submersible handle, and make it difficult for the lateral sleeve pipe drill to slip out of the passage of the submersible handle, thereby providing stable power for correcting the bone passage; on the other hand, it can effectively prevent the lateral sleeve pipe drill from centrifuging during a process of correcting the bone passage, thereby avoiding the formation of cone reaming, reducing damage to other tissues around a site that needs to be corrected, and reducing pain of a patient.

It should be noted that by arranging the fixing portion, on the one hand, the lateral sleeve pipe drill is not easy to slide during the process of correcting the bone passage, thereby ensuring that the lateral sleeve pipe drill can effectively ream, shortening a surgery time, and increasing the safety of the surgery. On the other hand, it is ensured that the lateral sleeve pipe drill is not easy to slip out of the passage of the handle body 2.

For the fixing portion, a plurality of structures and a plurality of arrangements can be provided. For example, a first groove 6 may be provided on an inner wall of the central passage 5 and the first groove 6 may be arranged in a direction parallel to a central axis of the central passage 5. By placing the lateral sleeve pipe drill in the first groove 6, the lateral sleeve pipe drill is fixed. In order to enhance the fixing effect, an interference fit is selected between the lateral sleeve pipe drill and the first groove 6.

Exemplarily, the fixing portion may not be provided on the central passage 5, and only a buckle is provided on a side wall of the lateral sleeve pipe drill in one direction. The buckle is adapted to the shape of the C-shaped central passage and is configured to fix the lateral sleeve pipe drill and the submersible handle.

In addition, a C-shaped buckle can also be arranged on an inner wall of the central passage 5 to fix the lateral sleeve pipe drill, alternatively, a fixing buckle 9 can be arranged on an outer wall of the lateral sleeve pipe drill, and a second groove (not shown in the figure) that is compatible with the fixing buckle is provided on the inner wall of the central passage to fix the lateral sleeve pipe drill, thereby ensuring effective reaming, shortening a surgery time, and increasing the safety of the surgery.

Figure 11:
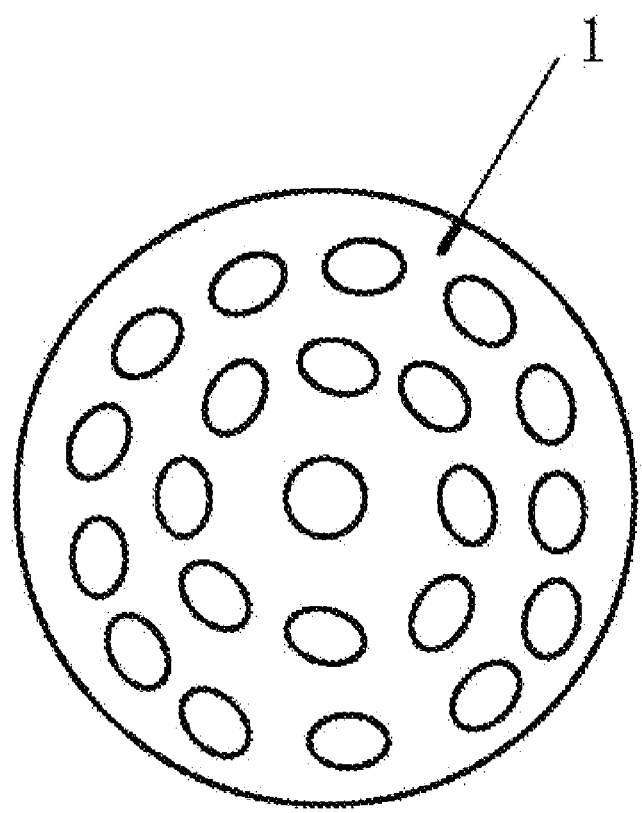
FIG. 11 is a top view of a hemispherical-type grip portion of a submerged handle.
Figure 12:
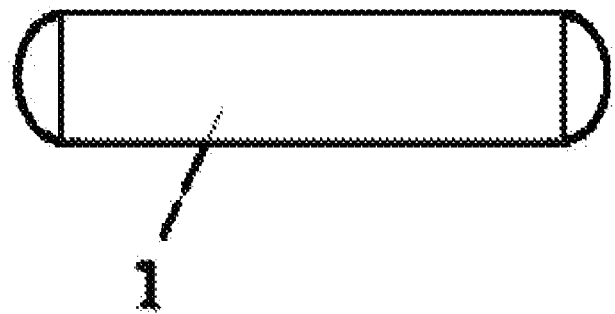
FIG. 12 is a top view of a straight line-shaped-type grip portion of a submersible handle.

In order to facilitate holding, in this embodiment, the grip portion is designed in a straight line-shape or a hollow hemispherical shape, as shown in FIGS. 11-12. Through the forgoing design, on the one hand, the lateral sleeve pipe drill is easy to be operated during the surgery, on the other hand, a torque and a moment arm are increased, the labor intensity of correcting the bone passage is reduced, the reaming speed is increased, and the surgery time is shortened.

Considering that during the surgery, the grip portion may block a field of vision. Therefore, in this embodiment, the grip portion is selected as a piercing hemispherical shape, or a material of the grip portion is selected as a transparent material. The forgoing design is convenient for observing the position and status of the lateral sleeve pipe drill during a reaming process.

Considering that if the material of the grip portion or the passage is a flexible or elastic material, the deformation of the material during the surgery affects the ability of the submersible handle to provide power for the lateral sleeve pipe drill. Therefore, in this embodiment, The material of the grip portion and the passage are both made of a hard plastic or a stainless steel. The forgoing design can effectively prevent ability of the submersible handle to provide power for the lateral sleeve pipe drill because a deformation of the passage during the reaming process is reduced, thereby ensuring that the submersible handle can provide stable and strong power for the lateral sleeve pipe drill.

The forgoing is only preferred specific implementations of the present disclosure, but the scope of protection of the present disclosure is not limited thereto. The person skilled in the art can easily think of changes or replacements within the technical scope disclosed in the present disclosure, which shall be covered within the scope of protection of the present disclosure.

What is claimed is:

1. A lateral sleeve pipe drill, wherein the lateral sleeve pipe drill is of a hollow cylindrical shape and comprises a first end and a second end, an outer wall of the first end is provided with a correction portion for correcting a bone passage, the first end is configured to be arranged in a human body and is of a shape adapted to different surgical methods, a surgical approach direction, and an internal structure of the human body; the second end is provided with a submersible handle to supply power to correct the bone passage, the submersible handle comprises a grip portion and a handle body, the handle body is provided with a passage into which the lateral sleeve pipe drill enters, a side wall of the handle body is provided with an opening through which the lateral sleeve pipe drill enters the passage, and the lateral sleeve pipe drill is partially arranged in the submersible handle; the passage comprises an oblique passage and a central passage arranged coaxially, the oblique passage and the central passage are arranged in a spiral structure in sequence; and the central passage has a C-shaped cross-section; at least one of the central passage and the lateral sleeve pipe drill is provided with a fixing portion, and the fixing portion is configured to fix the lateral sleeve pipe drill and the submersible handle.

2. The lateral sleeve pipe drill as claimed in claim 1, wherein the shape is of oblique-type.

3. The lateral sleeve pipe drill as claimed in claim 2, wherein the correction portion is one of a one-way thread, a cross-thread and emery.

4. The lateral sleeve pipe drill as claimed in claim 1, wherein the correction portion is one of a one-way thread, a cross-thread and emery.

5. The lateral sleeve pipe drill as claimed in claim 4, wherein the one-way thread is a horizontal thread or an oblique thread.

6. The lateral sleeve pipe drill as claimed in claim 1, wherein an inner wall of the central passage is provided with a groove for accommodating and fixing the lateral sleeve pipe drill, and the groove is arranged in a direction parallel to a central axis of the central passage.

7. The lateral sleeve pipe drill as claimed in claim 1, wherein a side wall of the lateral sleeve pipe drill in one direction is provided with a buckle adapted to a shape of the passage, and the buckle is configured to fix the lateral sleeve pipe drill and the submersible handle.

* * * * *